US011278504B1

(12) United States Patent
Sharif Naeini et al.

(10) Patent No.: US 11,278,504 B1
(45) Date of Patent: Mar. 22, 2022

(54) TREATMENT OF A LIONFISH STING AND FORMULATIONS FOR USE THEREOF

(71) Applicant: PteroTech Inc., Westmount (CA)

(72) Inventors: Reza Sharif Naeini, Candiac (CA); Stephanie Mouchbahani Constance, Westmount (CA)

( * ) Notice: Subject to any disclaimer, the term of this patent is extended or adjusted under 35 U.S.C. 154(b) by 0 days.

(21) Appl. No.: 16/856,688

(22) Filed: Apr. 23, 2020

Related U.S. Application Data (60) Provisional application No. 62/951,250, filed on Dec. 20, 2019.

(51) Int. Cl.

| | |
|---|---|
| *A61K 9/19* | (2006.01) |
| *A61K 31/122* | (2006.01) |
| *A61K 31/4965* | (2006.01) |
| *A61K 31/245* | (2006.01) |
| *A61K 31/167* | (2006.01) |
| *A61K 31/133* | (2006.01) |
| *A61K 31/505* | (2006.01) |
| *A61K 31/195* | (2006.01) |
| *A61K 31/675* | (2006.01) |
| *A61K 31/7076* | (2006.01) |
| *A61K 31/185* | (2006.01) |
| *A61K 31/7048* | (2006.01) |
| *A61P 39/02* | (2006.01) |
| *A61K 9/00* | (2006.01) |
| *A61K 47/18* | (2017.01) |

(52) U.S. Cl.
CPC .......... *A61K 31/122* (2013.01); *A61K 9/0014* (2013.01); *A61K 9/0019* (2013.01); *A61K 31/133* (2013.01); *A61K 31/167* (2013.01); *A61K 31/185* (2013.01); *A61K 31/195* (2013.01); *A61K 31/245* (2013.01); *A61K 31/4965* (2013.01); *A61K 31/505* (2013.01); *A61K 31/675* (2013.01); *A61K 31/7048* (2013.01); *A61K 31/7076* (2013.01); *A61K 47/183* (2013.01); *A61P 39/02* (2018.01)

(58) Field of Classification Search
CPC ..... A61P 39/02; A61K 31/122; A61K 9/0014; A61K 9/0019; A61K 31/133; A61K 31/167; A61K 31/185; A61K 31/195; A61K 31/245; A61K 31/4965; A61K 31/505; A61K 31/675; A61K 31/7048; A61K 31/7076; A61K 47/183
USPC .......................................................... 514/47
See application file for complete search history.

(56) References Cited

U.S. PATENT DOCUMENTS 9,005,628 B2 4/2015 Dolly et al.
2016/0375049 A1 12/2016 Miller

FOREIGN PATENT DOCUMENTS

CN 101879151 * 11/2010

OTHER PUBLICATIONS

Szanto et al. New P2X3 receptor antagonists. Part 2: Identification and SAR of quinazolinones. Bioorganic & Medicinal Chemistry Letters 26 (2016) 3905-3912. (Year: 2016).*
Glossary of medical education terms, Institute of International Medical Education. http://www.iime.org/glossary.htm Accessed in Mar. 2013. (Year: 2013).*
Diaz JH. Marine Scorpaenidae Envenomation in Travelers: Epidemiology, Management, and Prevention. Journal of Travel Medicine 2015; vol. 22 (Issue 4): 251-258. (Year: 2015).*
Mouchbahani-Constance et al. Lionfish venom elicits pain predominantly through the activation of nonpeptidergic nociceptors. PAIN 159 (2018) 2255-2266. Available online Jun. 29, 2018. (Year: 2018).*
Kabanova, et al. "Modulation of P2X3 Receptors by Spider Toxins", Biochimica et Biophysica Acta, vol. 1818, Issue 11, Nov. 2012, pp. 2868-2875.
Grishin et al., "Novel Peptide from Spider Venom Inhibits P2X3 Receptors and Inflammatory Pain". Annals of Neurology, 67(5), 680-683. May 2010.
Saez, et al. "Spider-Venom Peptides as Therapeutics". Toxins (Basel). Dec. 2010; 2(12): 2851-2871. Published online Dec. 20, 2010.
Krimon, et al. "P2X3 receptors induced inflammatory nociception modulated by TRPA1, 5-HT3 and 5-HT1A receptors". Pharmacology Biochemistry and Behaviour, vol. 112, Nov. 1, 2013, pp. 49-55.
Fernandes, et al., "The Functions of TRPA1 and TRPV1: Moving Away From Sensory Nerves", British Journal of Pharmaclogy, May 2012; 166(2): 510-521.
Mouchbahani-Constance, et al. "Lionfish Venom Elicits Pain Predominantly Through the Activation of Nonpeptidergic Nociceptors", PAIN, Nov. 2018—vol. 159—Issue 11—p. 2255-2266.
Zhang, et al. "Lys49 myotoxin from the Brazilian lancehead pit viper elicits pain through regulated ATP release", PNAS Mar. 21, 2017 114 (12) E2524-E2532; first published Mar. 6, 2017.

* cited by examiner

*Primary Examiner* — Yih-Horng Shiao
(74) *Attorney, Agent, or Firm* — Anglehart et al.

(57) ABSTRACT

A method of treating lionfish envenomation; it includes administering to a subject a therapeutically effective amount of a P2X3 receptor antagonist; topical compositions for treating lionfish envenomation are also described.

10 Claims, 7 Drawing Sheets

TREATMENT OF A LIONFISH STING AND FORMULATIONS FOR USE THEREOF

The present patent application claims priority from U.S. provisional patent application No. 62/951,250 filed on Dec. 20, 2019, incorporated herein by reference.

TECHNICAL FIELD

The present disclosure relates to the treatment of a lionfish sting, and more particularly to treating lionfish envenomation caused by the red lionfish (*Pterois volitans*).

BACKGROUND

Lionfish are a very invasive species in the Caribbean and throughout the Gulf of Mexico. They produce an excruciatingly painful sting for which there has been no effective treatment or cure.

The lionfish *Pterois volitans* is an invasive species that has taken over the entire Atlantic Coast of the United States of America, the Gulf of Mexico, as well as the Caribbean. In addition to the ecological impact of this invasion, the lionfish poses another very important problem: the dorsal spines it possesses and uses as a defense mechanism can deliver an extremely painful sting for which no treatment is available. The only reported remedy consists in immersing the affected limb in water as hot as possible for short periods of time in the hopes of denaturing the venom's peptides. This approach would provide a mild alleviation of the pain, and reduce its duration from days to hours.

The dorsally-directed spines of the lionfish can puncture the skin and deliver a very painful venom. The pain is intense and immediate. If left untreated, the disability produced by the pain, which leads to a state of persistent pain due to modifications of synaptic transmission in the spinal cord, can last up to one month (reference: Resiere et al.). It is therefore essential to treat the injury early on to prevent the pain from becoming persistent.

As such, it would be advantageous to discover a rapid and effective method or means of treating a person having been stung by a lionfish in order to reduce or eliminate the pain caused by its venom.

Moreover, as many different pathways and receptors are involved in causing pain as experienced by a subject, where the mechanism causing the pain may vary depending on the source resulting in the pain, identifying the pathway involved in pain experienced as a result of the lionfish venom is crucial in treating the pain with sufficient specificity as failure to do so may not alleviate symptoms caused by the venom.

SUMMARY

The present disclosure relates to methods of treating lionfish envenomation, having identified how the venom of this fish interacts with the nervous system of a subject to cause pain.

Many of the current forms of treatment lack efficacy as they do not target the pain pathway of the lionfish venom with sufficient specificity, the pain pathway of the lionfish venom having, prior to the present disclosure, yet to be discovered. Moreover, many of the current forms of treatment are not administered rapidly enough following envenomation, and/or fail to act sufficiently rapidly on the pain pathway used by the toxins of the venom to significantly alleviate symptoms.

The lionfish venom, once it enters the body of the subject, rapidly causes pain to the subject (e.g. see exemplary study 1). As such, it is important to administer an effective treatment rapidly to the subject (at least during the first two hours from the time of the sting, and preferably within the first 30 minutes from the time of the sting) in order to stifle the increase in pain (as the proteins of the venom bind to the relevant pain-related receptors of the subject).

Moreover, as the present disclosure discloses that the P2X3 receptor is a crucial receptor for causing the pain tied to the lionfish venom, and its blocking has an important impact on lowering or avoiding pain caused by the lionfish venom, the administration of a P2X3 receptor antagonist as a prophylaxis or within two hours following the sting effectively treats against lionfish envenomation (e.g. where re-administration of the P2X3 receptor antagonist may be necessary to pursue treatment until the presence of pain symptoms disappears). As such, effective compounds in treating lionfish envenomation demonstrate specificity for and are antagonists of the P2X3 receptor.

It has been discovered that the lionfish venom causes pain by predominantly activating a subset of pain-sensing fibers, also known as nociceptors. This subset is referred to as the non-peptidergic nociceptors.

However, as explained herein, the present disclosure relates to inhibiting or interacting with the receptor, using antagonists, that is involved in the pain-producing (algogenic) effect of the venom. The receptor is called P2RX3, or purinergic receptor subtype 3, also known as P2X3. It has been demonstrated that the venom activates human nociceptors via the P2X3 receptor. In nociceptors of a subject, blocking the P2X3 receptor prevents activation of the nociceptor.

Moreover, the present disclosure relates to a topical cream composition for reducing or eliminating the pain caused by the lionfish venom.

A broad aspect of the present disclosure is a method of treating lionfish envenomation comprising administering to a subject a therapeutically effective amount of a P2X3 receptor antagonist.

In some embodiments, the administering may be performed orally, parenterally and/or topically.

In some embodiments, the administering may be performed topically.

In some embodiments, the topical administration may be performed as a prophylaxis by applying a topical composition comprising the P2X3 receptor antagonist on one or both feet of the subject prior to the subject entering water where lionfish may be located.

In some embodiments, the antagonist of the P2X3 receptor may include a compound of the following formula:

or a pharmaceutically acceptable salt thereof.

In some embodiments, the lionfish may be of a species *Pterois volitans*.

In some embodiments, the antagonist may be administered within the first two hours following the lionfish envenomation.

In some embodiments, the antagonist may be administered within the first thirty minutes following the lionfish envenomation.

In some embodiments, the antagonist may be administered as a prophylaxis within an hour prior to the subject entering water where lionfish may be located.

In some embodiments, following the lionfish envenomation, the method may include at least one of disinfecting or applying an antiseptic to a site of the subject where the subject has been stung by the lionfish.

In some embodiments, following the lionfish envenomation, the method may include submerging a body part of the subject that has been stung by the lionfish in hot water of at least 40° C.

In some embodiments, the method may include re-administering, within two hours following a last administration of the P2X3 receptor antagonist, an additional therapeutically effective amount of the P2X3 receptor antagonist.

In some embodiments, following the lionfish envenomation, the administration may be performed by injection at or near a site where the subject was stung by the lionfish.

Another broad aspect is use of a P2X3 receptor antagonist for treating a subject from lionfish envenomation.

Another broad aspect is an antagonist of the P2X3 receptor for administration to a subject for treating the subject from lionfish envenomation.

Another broad aspect is a topical formulation for applying onto skin of a subject for treating lionfish envenomation. The formulation includes 2.0% (w/v)-5.0% (w/v) of Lidocaine or 5.0% (w/v)-20.0% (w/v) of Benzocaine; 1 mg/kg-10 mg/kg of Emodin; and 0.5% (w/v)-3.0% (w/v) of Tromethamine.

In some embodiments, the formulation may include EDTA used as a chelator.

In some embodiments, the formulation may include Lidocaine and not Benzocaine, and the concentration of Lidocaine is of 4% (w/v); wherein the concentration of Emodin may be of 5 mg/kg; and wherein the concentration of Tromethamine may be of 2% (w/v).

Another broad aspect is a method of treating lionfish envenomation by administering to a subject a therapeutically effective amount of one or more of (i)

[chemical structure]

or a pharmaceutically acceptable salt thereof;

(ii)

[chemical structure]

or a pharmaceutically acceptable salt thereof;

(iii)

[chemical structure]

or a pharmaceutically acceptable salt thereof;

(iv) 2',3'-O-(2,4,7-Trinitrocyclohexadienylidene) adenosine 5'triphosphate, or a pharmaceutically acceptable salt thereof;

(v)

[chemical structure]

or a pharmaceutically acceptable salt thereof;

(vi)

[chemical structure]

or a pharmaceutically acceptable salt thereof;

(vii)

or a pharmaceutically acceptable salt thereof;

(viii)

or a pharmaceutically acceptable salt thereof; and (ix)

or a pharmaceutically acceptable salt thereof;

(x)

or a pharmaceutically acceptable salt thereof; and (xi)

or a pharmaceutically acceptable salt thereof.

BRIEF DESCRIPTION OF THE DRAWINGS

The invention will be better understood by way of the following detailed description of embodiments of the invention with reference to the appended drawings, in which:

FIG. 3 includes graphs that show that the venom-elicited behavioral and cellular responses are independent of the TRPV1 or bradykinin (BK) receptors. (A) Mean (±SEM) spontaneous pain behavior quantified over a 1-hour period after intraplantar injection of 44 μg of venom in mice pretreated with a systemic (intraperitoneal) injection of saline (grey bar, n=5) or 0.1 μmol/kg of HOE-140 (white bar, n=5; Kruskal-Wallis 1-way ANOVA on ranks P=0.067). (B) Proportion of HEK293T cells responding to BK alone and in the presence of HOE-140 (black bars, n=21/85 and 0/85, respectively) and proportion of HEK293T cells responding to the venom alone and in the presence of HOE-140 (dark grey and light grey bars, 118/139 and 66/85 cells, respectively; Fisher exact test, P=0.939). (C) Sample traces of HEK293T cells showing a rise in intracellular calcium in response to a 1-second puff of BK (100 μM) and the reversible blockade of this response by the BK type 2 receptor HOE-140 (1 mM). (D) Mean (±SEM) spontaneous pain behavior quantified over a 1-hour period after intraplantar injection of 44 μg of venom in WT mice pretreated with a systemic (intraperitoneal) injection of vehicle (Veh, black bar, n=5) or 30 mg/kg AMG-9810 (white bar, n=5) (Kruskal-Wallis 1-way ANOVA on ranks, P=0.841 for the AMG group and P=0.862 for the TRPV1 KO group). (E) Proportion of cultured DRG neurons responding to capsaicin (Cap) alone and in the presence of AMG-9810 (black bars, n=45/65 and 0/65 cells, respectively) and proportion of cells responding to the venom alone and in the presence of AMG-9810 (dark and light grey bars, n=24/24 and 30/32, respectively; Fisher exact test, P=0.322). (F) Sample traces of DRG neurons (n=10 cells) showing a rise in intracellular calcium in response to a 1-second puff of capsaicin (Cap, 1 μM), a blocked response to a second puff of capsaicin after bathing cells in AMG-9810 (10 μM), and a response to a third puff of capsaicin after washing the antagonist of the dish. ANOVA, analysis of variance; DRG, dorsal root ganglion; WT, wild-type.

FIG. 4 includes graphs that illustrate representative calcium imaging traces demonstrating the rise in intracellular calcium produced by exposing nociceptors to the lionfish venom. Cultured mouse nociceptors were incubated with non-targeting (control) siRNA molecules. (B) The intracellular calcium responses elicited by the venom are absent in cultured mouse nociceptors treated with siRNA molecules against P2X3. The selective P2X3 receptor agonist α,β,Me-ATP also fails to elicit any calcium response in these nociceptors. The latter remain nonetheless excitable when depolarized with a high KCl solution. (C) Pharmacologically blocking P2X3 receptors with the selective antagonist AF-353 in cultured mouse nociceptors reversibly blocks the venom- and α,β,Me-ATP-elicited calcium responses. (D) Blockade of P2X3 receptors by Emodin also prevents nociceptors from getting activated by the lionfish venom.

DETAILED DESCRIPTION

The present disclosure relates to the treatment of lionfish envenomation, such as that caused by the species *Pterois volitans*, through the use of antagonists of the P2X3 receptor.

It has been determined that the receptor essential for the algogenic effect of the lionfish venom is the P2X3 receptor. Blocking the P2X3 receptor with an antagonist, such as the synthetic drug AF-353 ($C_{14}H_{17}IN_4O_2$), is effective in reducing or eliminating pain caused by the venom.

Furthermore, the natural extract product Emodin, which can be produced from several plants and roots, has been shown to have an inhibitory effect on the P2X3 receptor.

Venoms are composed of a cocktail of toxin molecules, each executing a different function and acting in concert to produce one final phenotype. Many venoms possess toxins that have specifically evolved to cause pain by activating a receptor on pain-sensing neurons to amplify pain signals for victims of envenomation. In the case of lionfish venom, it possesses a toxin that specifically targets the P2X3 receptor to cause pain. However, other venoms include toxins that act on different receptors to cause pain, such as $Na_v$s, $K_v$s, $Ca_v$s etc. and as such would require different pharmacological interventions to block the activation of nociceptors. Thus, by identifying the pathway by which a species' venom specifically causes pain, it is possible to design an effective pharmacological intervention for victims of envenomation by that species.

Definitions

In the present disclosure, by "agonist", it is meant a compound that increases the activity of another compound or receptor site.

In the present disclosure, by "antagonist", it is meant a compound that diminishes the activity of another compound or receptor site.

In the present disclosure, by "aminoalkyl", it is meant a C1-C7, saturated or unsaturated, linear or branched alkyl joined to an amino group ($NH_2$). Examples of aminoalkyl include, but are not limited to, —$CH_2NH_2$, —$CH_2CH_2NH_2$, etc. An aminoalkyl may be optionally substituted with one or more (e.g. one to five) substituents independently selected from, for instance, the group consisting of hydroxy, thiol, cyano, nitro, loweralkyl, sulfonyl, halogen or amino.

In the present disclosure, by "body part", it is meant a part of the body of the subject (e.g. foot, forearm, hand, thigh, etc.), including one or more specific muscles.

In the present disclosure, by "cycloalkyl", it is meant a three to ten membered monocyclic or polycyclic ring, saturated or partially unsaturated, where all of the ring atoms are carbon. Examples of cycloalkyl include, but are not limited to, cyclopropyl, cyclobutyl, cyclopentyl, cyclopentenyl, cyclohexyl, cyclohexenyl, etc. A cycloalkyl may be optionally substituted by one to five substituents independently selected from, for instance, the group consisting of hydroxy, thiol, cyano, nitro, loweralkyl, sulfonyl, halogen or amino.

In the present disclosure, by "lionfish envenomation", it is meant the injection process of the lionfish venom into the body of the subject (e.g. the venom delivered through the spine of the lionfish). The venom causes pain to the subject through a pathway involving the P2X3 receptor as described herein.

In the present disclosure, by "loweralkoxy" or "oxyalkyl", it is meant a C1-C7, saturated or unsaturated, linear or branched alkoxy, such as methoxy, ethoxy, propyloxy, butyloxy, isopropyloxy, and t-butyloxy. A loweralkoxy or oxyalkyl may be optionally substituted with one or more (e.g. one to five) substituents independently selected from, for instance, the group consisting of hydroxy, thiol, cyano, nitro, loweralkyl, sulfonyl, halogen or amino.

In the present disclosure, by "loweralkyl," it is meant a C1-C7, saturated or unsaturated (e.g. one or more double or triple bonds), linear or branched alkyl, such as methyl, ethyl, propyl, butyl, isobutyl, isopropyl, sec-butyl, tert-butyl, pentyl, isopentyl, and hexyl. A loweralkyl may be optionally substituted with one or more (e.g. one to five) substituents independently selected from, for instance, the group consisting of hydroxy, thiol, cyano, nitro, loweralkyl, sulfonyl, halogen or amino.

In the present disclosure, by "modulator", it is meant a compound that interacts with a target, and includes, for instance, agonists and/or antagonists.

In the present disclosure, by "pharmaceutically acceptable", it is meant that which is useful in preparing a pharmaceutical composition that is generally safe, non-toxic, and neither biologically or otherwise undesirable and includes that which is acceptable for at least human pharmaceutical use.

In the present disclosure, by "prophylaxis", it is meant a measure taken to avoid the pain, at least in part, caused by lionfish envenomation of the subject.

In the present disclosure, by "subject", it is meant a mammal, such as a human. The term "subject" should not bring on any limitations as to the sex or age.

In the present disclosure, by "therapeutically effective amount", it is meant an amount of a compound that, when administered to a subject for preventing pain, is sufficient to at least begin alleviating the pain symptoms. The "therapeutically effective amount" will vary on the compound that is being administered, the extent and number of lionfish stings, the condition of the subject (e.g. age, health, weight, sex), the route and form of administration, the species that stung the subject, etc.

In the present disclosure, by "treating" or "treatment", it is meant one or more of (i) preventing part of all of the pain caused by lionfish envenomation (temporarily or permanently), (ii) inhibiting or arresting part or all of the pain caused by lionfish envenomation (temporarily or permanently), and (iii) relieving part or all of the pain caused by lionfish envenomation (temporarily or permanently).

In the present disclosure, by "water where lionfish may be located", it is meant a body of water where a subject may encounter a lionfish, such as an ocean next to Atlantic Coast of the United States of America, the Gulf of Mexico, or in the Caribbean. A body of water may also include an aquarium, pool, basin, pond, etc.

Exemplary P2X3 Receptor Antagonists

Table 1 illustrates a list of exemplary P2X3 receptor antagonists that can be administered to reduce or eliminate pain caused by lionfish envenomation. However, it will be understood that the compounds presented in Table 1 are but exemplary P2X3 receptor antagonists. Moreover, optionally, the compounds presented in Table 1 may also be optionally substituted with one or more substitute groups (e.g. loweralkyl, loweralkoxy, aminoalkyl, cycloalkyl, mercapto, ciano, hydroxy, thiol, cyano, nitro, loweralkyl, sulfonyl, halogen, amino etc.)

As such, one or more these exemplary compounds may be administered to treat lionfish envenomation.

TABLE 1

Exemplary compounds that can act as P2X3 receptor antagonists for treating lionfish envenomation.

| # | Name | Nomenclature or Structure |
|---|------|---------------------------|
| 1 | AF-353 |  |
| 2 | Emodin |  |
| 3 | A-317491 |  |

TABLE 1-continued

Exemplary compounds that can act as P2X3 receptor antagonists for treating lionfish envenomation.

| # | Name | Nomenclature or Structure |
|---|------|---------------------------|
| 4 | TNP-ATP | 2',3'-O-(2,4,7-Trinitrocyclohexadienylidene) adenosine 5'triphosphate |
| 5 | PPADS |  |
| 6 | AF-219 |  |
| 7 | AF-906 |  |
| 8 | Ro 3 |  |

TABLE 1-continued

Exemplary compounds that can act as P2X3 receptor antagonists for treating lionfish envenomation.

| # | Name | Nomenclature or Structure |
|---|------|---------------------------|
| 9 | Suramin |  |
| 10 | Tetramethylpyrazine |  |
| 11 | Puerarin |  |

In some examples, the sources of Emodin may be synthetic, or as an extract from any of the following emodin-producing plants: *Acalypha australis, Cassia occidentalis, Cassia siamea, Frangula alnus, Glossostemon bruguieri, Kalimeris indica, Polygonum hypoleucum, Reynoutria japonica, Rhamnus alnifolia, Rhamnus cathartica, Rheum palmatum, Rumex nepalensis, Senna obtusifolia, Thielavia subthermophlla, Ventilago madraspatana.*

Exemplary P2X3 Receptor Antagonists Topical Formulations

The following provides a list of exemplary P2X3 receptor antagonist topical formulations in accordance with the present teachings for treating lionfish envenomation of a subject. It will be understood that the following exemplary topical formulations are but illustrative, and that other topical formulations may be used in accordance with the present teachings.

The topical formulation can be applied at the site of the sting to block the venom's receptor (e.g. Emodin) and reduce nociceptor excitability (e.g. lidocaine). Such application may block nociceptor activation in the minutes that follow the sting, if applied, and will prevent the long-lasting debilitating effects of the venom.

A first topical formulation for treating lionfish envenomation may include Lidocaine (2-5% (w/v)—in some examples, 4% (w/v)), Tromethamine (0.5-3% (w/v)—in some examples, 2% (w/v)), EDTA, and one or more P2X3 receptor antagonists.

A second topical formulation for treating lionfish envenomation may include Lidocaine (2-5% (w/v)—in some examples, 4% (w/v)), acetylsalicylic acid (32.5% (w/v)), EDTA and one or more P2X3 receptor antagonists.

A third topical formulation for treating lionfish envenomation may include Benzocaine (5-20% (w/v)—in some examples 15% (w/v)), tromethamine (0.5-3% (w/v)—in some examples, 2% (w/v)), EDTA and one or more P2X3 receptor antagonists.

A fourth topical formulation for treating lionfish envenomation may include Benzocaine (5-20% (w/v)—in some examples 15% (w/v)), acetylsalicylic acid (32.5% (w/v)), EDTA and one or more P2X3 receptor antagonists.

A fifth exemplary formulation for treating lionfish envenomation may include lidocaine (2-5% (w/v)—in some examples, 4% (w/v)), which would block activity in nociceptors. Lidocaine alone, however, may not be sufficient to block nociceptor activation by the venom. The main target of the latter being the P2X3 receptor, the formulation may also contain Emodin (1-10 mg/kg—in some examples, 5 mg/kg) as a non-medicinal ingredient, tromethamine (0.5-3% (w/v)—in some examples, 2% (w/v)) as an anti-inflammatory and EDTA as a chelator.

A sixth exemplary formulation may include the following ingredients in the following doses: Lidocaine (4% (w/v)), EDTA (200 µM), Emodin (5 mg/kg), Tromethamine (2% (w/v)), dissolved in physiological saline.

It will be understood that the above exemplary are non-exhaustive and non-limiting, and may include other compounds such as one or antibiotics, anti-inflammatories, antiseptics, etc.

Administration and Pharmaceutical Compositions:

The P2X3 receptor antagonists of the present disclosure may be administered as a compound or a pharmaceutically acceptable salt or solvate of the composition, accompanied with at least one therapeutically acceptable carrier, and optionally one or more additional ingredients (e.g. an antibiotic, antiseptic, prophylactic, therapeutic compound, etc.). The additional ingredients (e.g. an antibiotic, antiseptic, prophylactic, therapeutic compound, etc.) may be part of the same mixture that includes the P2X3 antagonist, or supplied separately, such as in a kit made available to a medical practitioner or the subject.

The P2X3 receptor antagonists may be administered in a therapeutically effective amount by different acceptable modes, depending on the nature of the P2X3 receptor antagonists and the accepted mode of administration for that P2X3 receptor antagonists. A person of ordinary skill in the art will be able to ascertain, without undue experimentation and based on the disclosure provided herein and common general knowledge, the therapeutically effective amount for a particular P2X3 receptor antagonist.

The P2X3 receptor antagonists may be administered as pharmaceutical compositions in such manners that include, but are not limited to, oral, topical, parenteral (i.e. injection), subcutaneous, intravenous, nasal, etc. The administration of the pharmaceutical compositions may be performed through a spray.

For parenteral administration, the solutions may be in such forms as suspensions, solutions or emulsions. Examples of carriers may be, for instance, propylene glycol, polyethylene glycol organic esters. Other agents may be added such as one or more wetting, wetting, emulsifying, suspending, stabilizing and dispersing agents.

The topical forms of administration may be, for instance, ointments, sprays, creams or lotions, or a transdermal patch, and may be oil or aqueous-based. The composition may include one or more emulsifying agents, thickening agents, etc.

The subject may take a therapeutically effective amount of the P2X3 receptor antagonist as a prophylaxis. As exemplified in exemplary study 1 as described herein, a therapeutically effective amount of the P2X3 receptor antagonist used as a prophylaxis may be taken anywhere within the hour prior to lionfish envenomation. As such, if the subject were to be exposed to waters that contain lionfish, or where there is a risk of contact with a lionfish (e.g. Atlantic Coast of the United States of America, the Gulf of Mexico, as well as the Caribbean's), the subject may be administered (e.g. take or apply) a therapeutically effective amount of the P2X3 receptor antagonist within the hour prior to entering the water.

Taking a therapeutically effective amount of the P2X3 receptor antagonist within the hour prior to lionfish envenomation has shown to at least reduce the pain experienced as a result of lionfish envenomation.

For instance, if the therapeutically effective amount of the P2X3 receptor antagonist is in a topical form, the subject may apply the topical formula to one or more body parts (e.g. to one or both bases of the subject's feet—as the subject may risk stepping onto a lionfish when present in the water) where the subject risks coming into contact with a spine of the lionfish. Similarly, if the therapeutically effective amount of the P2X3 receptor antagonist is administered orally, such oral administration may also be performed within an hour prior to a risk or envenomation.

The therapeutically effective amount of the P2X3 receptor antagonist may also be retaken every hour or so during the course of time a subject is exposed to the waters. It will be understood that the amount of times the subject will have to re-administer the therapeutically effective amount of the P2X3 receptor antagonist depends on such factors as the nature of the P2X3 receptor antagonist, the characteristics of the subject (e.g. age, weight, health, sex, etc.), the amount of the initial dose, the mechanism of administration (e.g. topical, oral, etc.), etc.

The therapeutically effective amount of the P2X3 receptor antagonist may also be administered after lionfish envenomation (e.g. the subject being stung by the spine of the lionfish). The therapeutically effective amount of the P2X3 receptor antagonist may be preferably administered within two hours following the lionfish envenomation. However, in some embodiments, it may be preferable to administer the therapeutically effective amount of the P2X3 receptor antagonist within the first 30 minutes following the lionfish envenomation (e.g. prior to the pain caused by the lionfish venom reaching its peak).

The time of administration is important, as described herein, as it allows the P2X3 receptor antagonist to interact with the P2X3 receptor, thereby reducing the pain prior to the appearance of worsening of the pain. It is shown that administration of the therapeutically effective amount of the P2X3 receptor antagonist may be administered within two hours following lionfish envenomation, or preferably within 30 minutes from lionfish envenomation, in order to reduce or avoid the pain caused by lionfish envenomation.

In some examples where the subject has been stung by the lionfish, it may be advantageous to apply a disinfectant as is known in the art (e.g. antibiotic or antiseptic) at and/or next to the place of the wound.

In some examples where the subject has been subject to lionfish envenomation, it may be preferable to place the affected body part (e.g. arm, foot, etc.) in a body of hot water in order to encourage denaturing of the protein that compose the lionfish venom, in order to reduce the pain.

In some examples where a therapeutically effective amount of the P2X3 receptor antagonist has been administered to a subject following lionfish envenomation, the therapeutically effective amount of the P2X3 receptor antagonist may also be retaken every hour or so following the intake of the first therapeutically effective amount. It will be understood that the amount of times the subject will have to re-administer the therapeutically effective amount of the P2X3 receptor antagonist depends on such factors as the nature of the P2X3 receptor antagonist, the characteristics of the subject (e.g. age, weight, health, sex, etc.), the amount of the initial dose, the mechanism of administration (e.g. topical, oral, etc.), etc.

In some examples where the therapeutically effective amount of the P2X3 receptor antagonist is administered topically following lionfish envenomation, the topical formulation may be applied to the subject at or near the site where the lionfish venom has entered the body of the subject (i.e. the site where the subject has been stung by the spine of the lionfish).

In some examples where the therapeutically effective amount of the P2X3 receptor antagonist is administered parenterally following lionfish envenomation, the parenteral administration (e.g. injection) may be performed at or near the site where the lionfish venom has entered the body of the subject (i.e. the site where the subject has been stung by the spine of the lionfish).

Exemplary Studies:

The following exemplary studies are provided to enable the skilled person to better understand the present disclosure. As they are but illustrative and representative examples, they should not limit the scope of the present disclosure, only added for illustrative and representative purposes. It will be understood that other exemplary studies may be used to further illustrate and represent the present disclosure without departing from the present teachings.

Exemplary Study 1:

The time of presentation and disappearance of pain caused by the venom of a lionfish was first studied.

Venom was extracted from the dorsal spines of freshly euthanized lionfish, purified using published protocols (see Mouchbahani-Constance et al., PAIN 2018).

Protein concentration in the venom extract was determined to be 2.2 µg/µL using the Bio-Rad DC assay. Mice (12-weeks old C57BL/6 males and females, The Jackson Laboratory) were placed in an observation chamber on a glass platform, under which a mirror was placed at a 45° angle so as to show the hind paw of the mouse to the recording videocamera. Once the mice were acclimatized to the chamber, they were taken out and injected in the ventral aspect of their left hind paw with a 20 µl solution of the crude or diluted venom (44 or 4.4 µg/20 µl). The venom was extracted in sterile physiological saline (0.9% NaCl) and the same vehicle was used for dilutions. The behavioral displays of pain, assessed as the time spent by the mouse licking the injected paw, were recorded for a period of 1 hour after the injection. The data demonstrates the pain behavior, quantified as the time spent licking the injected paw, caused by injection of the lionfish venom at different protein concentrations (originally published in Mouchbahani-Constance et al., PAIN 2018).

Figure 1:
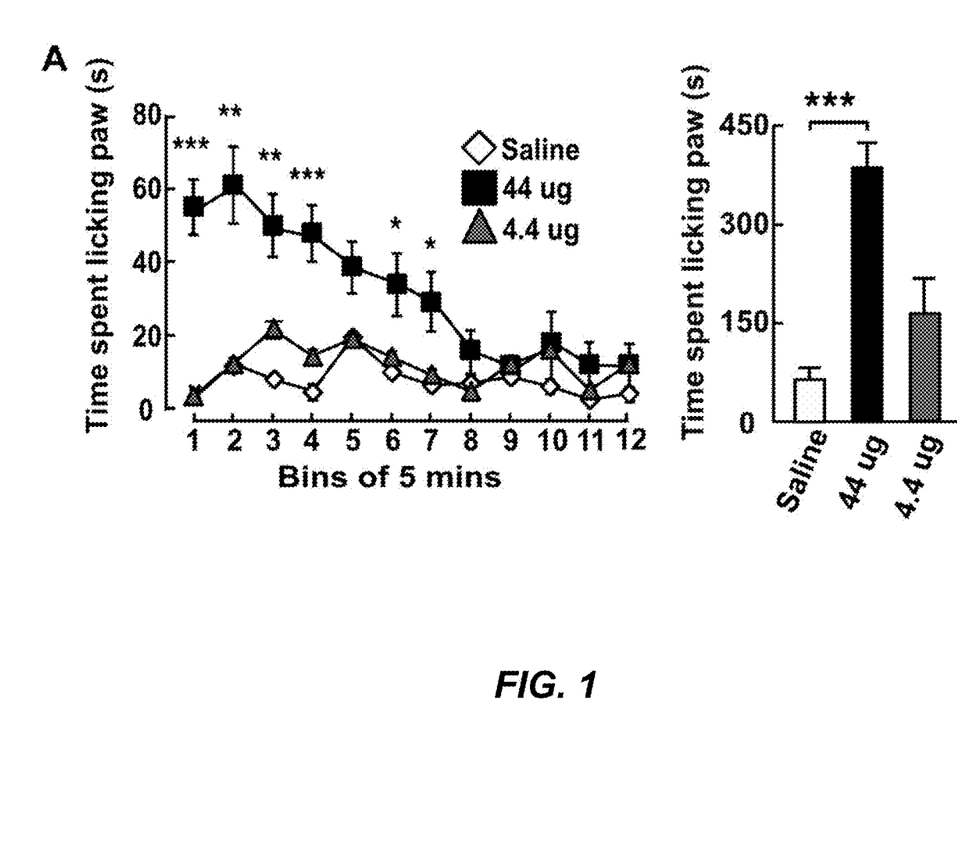
FIG. 1 includes graphs illustrating that lionfish venom injection elicits sustained spontaneous pain behavior. (A) Mean (±SEM) duration of spontaneous pain behavior assessed for 1 hour after the intraplantar injection of 44 μg (n=12; dark grey symbols), 4.4 μg (n=6; light grey symbols), or 0 μg (saline; n=5; blue symbols) of venom. Left: spontaneous pain behavior 1 hour immediately after injection, divided into 5-minute bins. Right: sum of the time spent displaying spontaneous pain behavior in the 1 hour immediately after the injection.

The data presented in FIG. 1 demonstrates how the lionfish venom injection elicits sustained spontaneous pain behavior. At (A), the mean (±SEM) duration of spontaneous pain behavior assessed for 1 hour after the intraplantar injection of 44 µg (n=12; dark grey symbols), 4.4 µg (n=6; light grey symbols), or 0 µg (saline; n=5; blue symbols) of venom is shown. Left: spontaneous pain behavior 1 hour immediately after injection, divided into 5-minute bins. Right: sum of the time spent displaying spontaneous pain behavior in the 1 hour immediately after the injection.

The results show that the pain experienced is immediate, increases in intensity in the following 10 minutes, and gradually dies down in the course of the following hour. In humans stung by the lionfish, the pain is intense in the beginning, increases in intensity over the following 30 minutes and peaks between 3-5 hours after the sting. If left untreated, the disability produced by the pain, which leads to a state of persistent pain due to modifications of synaptic transmission in the spinal cord, can last up to one month (reference: Resiere et al.). It is therefore essential to treat the injury early on to prevent the pain from becoming persistent.

Exemplary Study 2:

It was then determined which set of neurons are activated by the venom.

for in vitro calcium imaging experiments, Cre-dependent GCaMP6f mice (Ai95D; Jackson Labs) were crossed with Advillin-Cre mice (provided by Fan Wang, Duke University). GCaMP6f is a genetically-encoded calcium sensor and Advillin is a gene expressed by all sensory neurons. Dorsal root ganglion (DRG) neurons were cultured as previously described (Malin et al., Nature Protocols 2007). Briefly, 6 DRGs were dissected from adult (8-12 weeks old) mice in sterile Hank solution at 4° C. and mechanically dissociated by trituration. A low-density culture of sensory neurons was plated onto poly-D lysine-coated coverslips with Neurobasal media (Gibco 21103-049) supplemented with 1% FBS, B-27 supplement (Thermo-Fisher 17504-044), and 0.5-mM L-glutamine (Gibco 25030-081). Coverslips were maintained in a 34° C. incubator with 7% $CO_2$ and maintenance media (same as plating media without FBS) changed every 3 to 4 days. Neurons were tested 5 to 10 days after plating.

For experimental testing, a coverslip was transferred to a recording chamber perfused at 2 mL/minute with oxygenated (95% $O_2$-5% $CO_2$) room temperature artificial cerebrospinal fluid containing (in mM) 126 NaCl, 2.5 KCl, 2 $CaCl_2$), 2 MgCl2, 10 D-glucose, 26 $NaHCO_3$, and 1.25 NaH2PO4. An aliquot of venom was thawed daily and loaded into a glass puff pipette (8-MΩ resistance). The tip of the pipette was positioned 5 µm above the coverslip, 50 to 70 µm upstream of the cells to be analyzed. Venom was applied as a 2-second long puff at 2 PSI using a picospritzer (Toohey Company, Fairfield, N.J.) while monitoring responses as described below. To determine whether the nociceptors were of the peptidergic category, 1-µM capsaicin was dripped into the recording chamber, upstream of the imaged neurons. Calcium-dependent changes in GCaMP6f fluorescence were monitored using a NeuroCCD-SM256 imaging system (RedShirt Imaging, Decatur, Ga.) mounted on a Zeiss AxioExaminer microscope with filter set 46HE and a 40× water immersion objective (0.75 NA). Images were acquired at 50 Hz with a 10× digital gain. Image analysis was performed by drawing a region of interest around individual neurons. All Ca2+ imaging traces are background subtracted (using an adjacent region without GCaMP signal) and expressed as change in region of interest fluorescence intensity normalized by baseline fluorescence intensity (ie, $\Delta F/F$).

Figure 2:
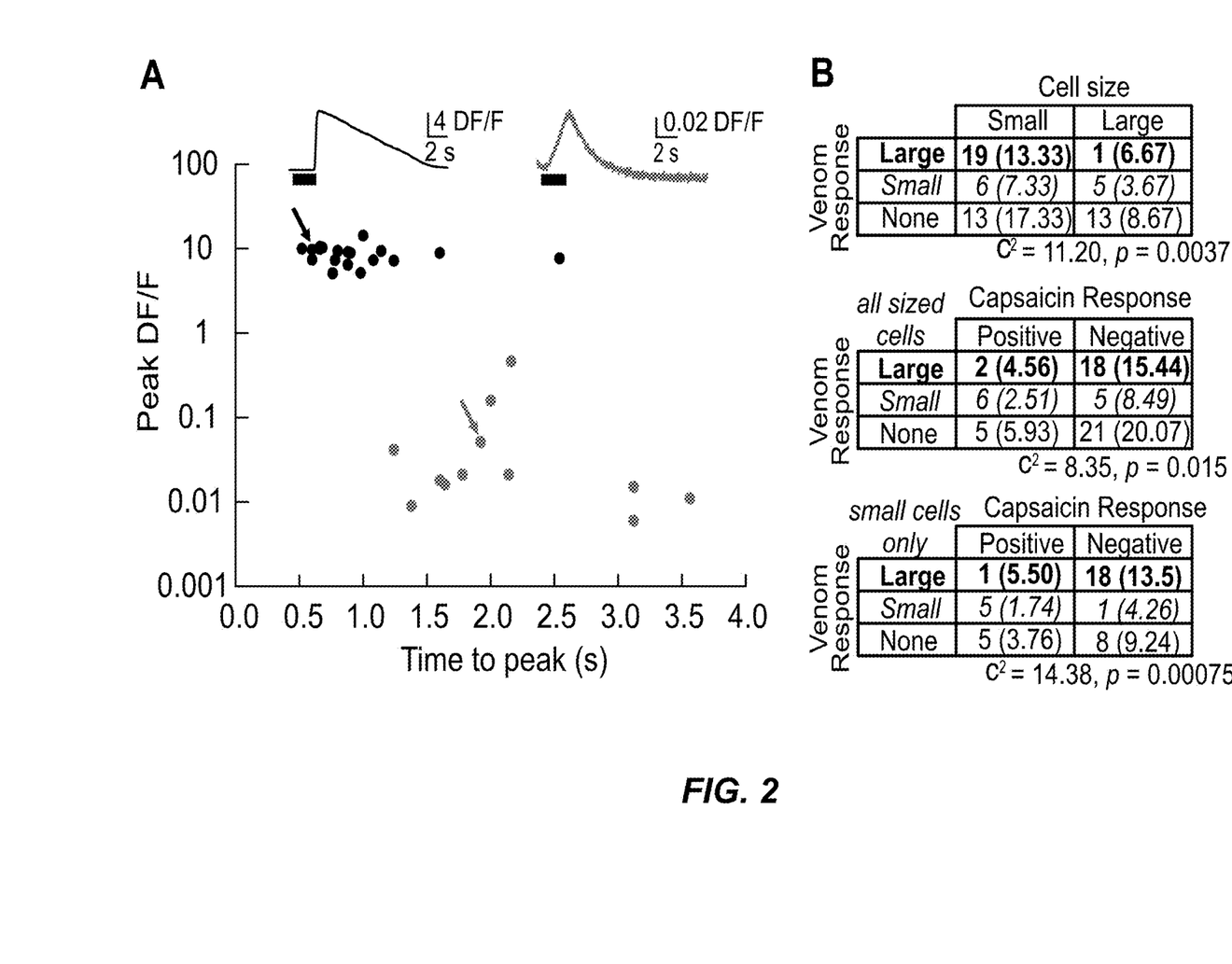
FIG. 2 includes graphs that show that the lionfish venom predominantly excites non-peptidergic nociceptors. (A) Inset: sample GCaMP fluorescence responses to venom application (black bar). Peak 4F/F and latency to peak from response onset were measured for each cell based on first venom application. Venom responses fell into 3 groups: large, abrupt-onset response (top-left cluster, black symbols); small, gradual-onset response (lower cluster, grey symbols); no response (not shown). Note difference between vertical scale bars for black and grey sample responses; data point for each response is highlighted by arrow. (B) Tables show observed (expected) number of cells showing each type of venom response, subdivided according to cell size (top) and capsaicin sensitivity (middle and bottom).

The data in FIG. 2 demonstrate that the venom activates predominantly one type of sensory neurons. Panel B (top table) indicates that only small diameter sensory neurons are activated by the venom. These are almost all nociceptors. The third table demonstrates that among nociceptors (small sized cells), those with a large calcium response to the venom were unresponsive to capsaicin, an agonist of peptidergic nociceptors. This indicates that non-peptidergic nociceptors are responsible for the venom's algogenic effect.

As shown in FIG. 2, lionfish venom predominantly excites non-peptidergic nociceptors. Peak $\Delta F/F$ and latency to peak from response onset were measured for each cell based on first venom application. Venom responses fell into 3 groups: large, abrupt-onset response (top-left cluster, black symbols); small, gradual-onset response (lower cluster, grey symbols); no response (not shown). The difference between vertical scale bars for black and grey sample responses is noted. The data point for each response is highlighted by an arrow. (B) Tables show observed (expected) number of cells showing each type of venom response, subdivided according to cell size (top) and capsaicin sensitivity (middle and bottom). As expected, large cells did not respond to capsaicin, hence bottom table shows relationship between venom response and capsaicin response based only on small cells. To summarize, the cells exhibiting large venom responses were disproportionately small and TRPV1-negative.

Exemplary Study 3:

It was then further demonstrated which receptors are involved in the pain pathway involving the lionfish venom.

Figure 3:
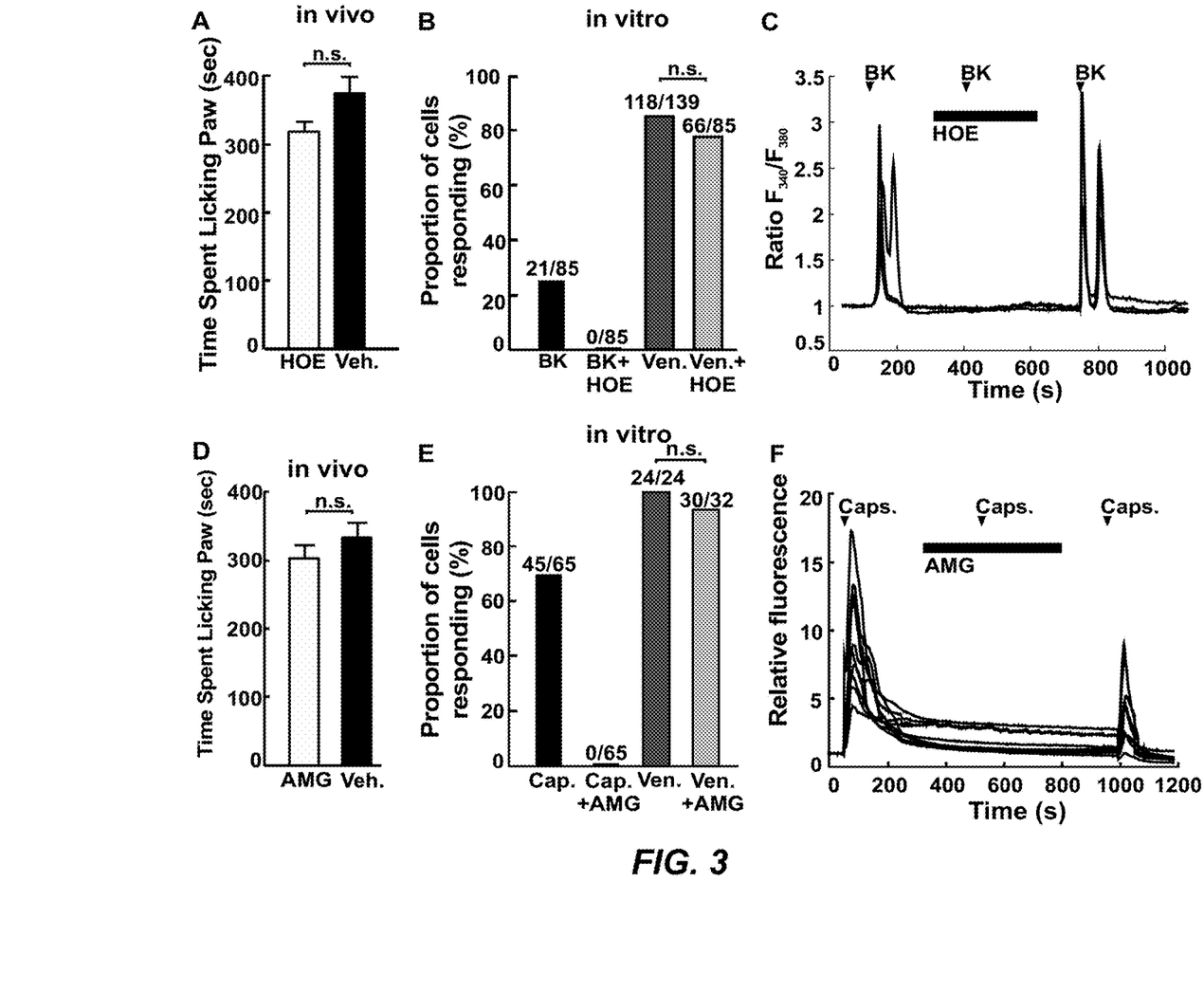

FIG. 3 demonstrates that the algogenic effect of the venom does not come from the activation of other receptors known to be involved in the pain pathway: the capsaicin receptor TRPV1 or the bradykinin receptor.

To test the bradykinin B2 receptor antagonist, changes in the intracellular calcium concentration in single cells were measured with the fluorescent Ca2+ indicator Fura-2. The latter was intermittently excited by 340- and 380-nm light every 2 seconds using a Fura-2 dichroic filter cube (Chroma Technology, Bellows Falls, Vt.) and a 40× water-immersed objective (Olympus, Tokyo, Japan). A 510/80 band-pass emission filter (Chroma Technology) was used, so that the appropriate 510-nm emission light may be collected by a CoolSNAP MYO camera (Photometrics, Tucson, Ariz.). Metafluor software (Molecular Devices Version 7.7) was used for data acquisition. HEK293T cells were loaded with 2 µM of Fura-2 acetoxymethylester in normal EC solution (in mM: NaCl 150, KCl 3, Glucose 10, $CaCl_2$) 2, and MgCl2 1; in distilled water, buffered to a pH of 7.3) for 1 hour before imaging. Cells were washed 3 times with EC saline solution before and after loading. Cells were continuously superfused with EC media at a flow rate of 2 to 3 mL/minute. Both EC media and HOE-140 (1 mM) were applied through a fast solution exchanger (Harvard Apparatus #SF-77B). For recordings, cells were imaged every 2 seconds at 40× magnification, and the ratio of the fluorescent signals (F340/F380) was used to determine changes in intracellular calcium concentrations. Bradykinin (100 µM) and crude lionfish venom were applied during 1 second over the imaging region. Cell responses to puff applications were considered positive when the intracellular calcium concentration rose by at least 20% over baseline values within 20 seconds after the application.

To test the TRPV1 receptor antagonist, changes in intracellular calcium concentrations in single cells were recorded as changes in GCaMP6f fluorescence. Exposure to the antagonist (10 µM) and image analysis were performed in a manner similar to the bradykinin (BK) receptor antagonist described above. The TRPV1 receptor agonist capsaicin (1 µM) and lionfish venom were applied during 1 second over the imaging region.

As shown in FIG. 3, venom-elicited behavioral and cellular responses are independent of the TRPV1 or bradykinin (BK) receptors. (A) Mean (±SEM) spontaneous pain behavior quantified over a 1-hour period after intraplantar injection of 44 µg of venom in mice pretreated with a systemic (intraperitoneal) injection of saline (grey bar, n=5) or 0.1 µmol/kg of HOE-140 (white bar, n=5; Kruskal-Wallis 1-way ANOVA on ranks P=0.067) is shown. (B) Proportion of HEK293T cells responding to BK alone and in the presence of HOE-140 (black bars, n=21/85 and 0/85, respectively) and proportion of HEK293T cells responding to the venom alone and in the presence of HOE-140 (dark grey and light grey bars, 118/139 and 66/85 cells, respectively; Fisher exact test, P=0.939) is shown. (C) Sample traces of HEK293T cells showing a rise in intracellular calcium in response to a 1-second puff of BK (100 µM) and the reversible blockade of this response by the BK type 2 receptor HOE-140 (1 mM) is shown. (D) Mean (±SEM) spontaneous pain behavior quantified over a 1-hour period after intraplantar injection of 44 µg of venom in WT mice pretreated with a systemic (intraperitoneal) injection of vehicle (Veh, black bar, n=5) or 30 mg/kg AMG-9810 (white bar, n=5) (Kruskal-Wallis 1-way ANOVA on ranks, P=0.841 for the AMG group and P=0.862 for the TRPV1 KO group) is shown. (E) Proportion of cultured DRG neurons responding to capsaicin (Cap) alone and in the presence of AMG-9810 (black bars, n=45/65 and 0/65 cells, respectively) and proportion of cells responding to the venom alone and in the presence of AMG-9810 (dark and light grey bars, n=24/24 and 30/32, respectively; Fisher exact test, P=0.322) is shown. (F) Sample traces of DRG neurons (n=10 cells) showing a rise in intracellular calcium in response to a 1-second puff of capsaicin (Cap, 1 µM), a blocked response to a second puff of capsaicin after bathing cells in AMG-9810 (10 µM), and a response to a third puff of capsaicin after washing the antagonist of the dish is shown.

Exemplary Study 4:

It was then demonstrated what was the cause of the excitation caused by the venom on the nociceptors.

Figure 4:
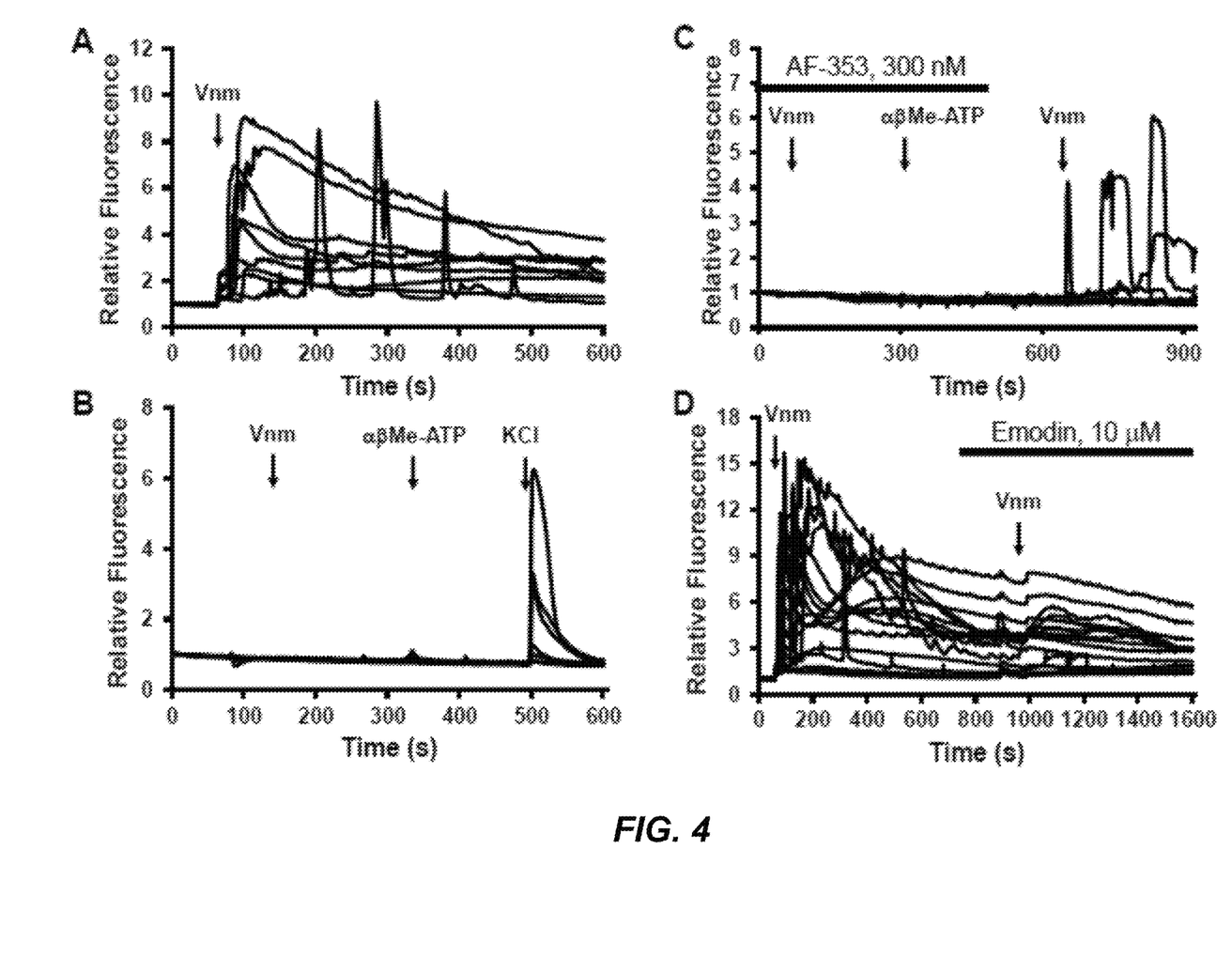

FIG. 4 demonstrates that the excitation that the venom causes on nociceptors comes from the activation of P2X3 receptors.

Cre-dependent GCaMP6f mice (Ai95D; Jackson Labs) were crossed with TRPV1-Cre mice to express GCaMP6f in all nociceptors. In TRPV1-Cre::GCaMP6f mice, GCaMP6f expression is not limited to cells that are TRPV1-positive at maturity, because TRPV1 is expressed broadly amongst nociceptors early in development. As with all other experiments described here, these were performed in a blinded fashion, so that the experimenter performing the behavioral tests was not aware of the venom concentration or the treatment conditions.

DRG cultures were grown on 35 mm dishes. On the 3rd day, the cultures were treated with complexes of predesigned siRNA molecules directed against mouse P2X3 or a non-targeting control siRNA (Qiagen FlexiTube siRNA final concentration 100 nM) and 2 ul of HiPerFect transfection reagent. The cells were incubated with the transfection complexes for 48 to 72 hours with addition of fresh media 24 h post-transfection.

FIG. 4 shows, at (A), representative calcium imaging traces demonstrating the rise in intracellular calcium produced by exposing nociceptors to the lionfish venom. Cultured mouse nociceptors were incubated with non-targeting (control) siRNA molecules. At (B), the intracellular calcium responses elicited by the venom are absent in cultured mouse nociceptors treated with siRNA molecules against P2X3. The selective P2X3 receptor agonist α,β,Me-ATP also fails to elicit any calcium response in these nociceptors. The latter remain nonetheless excitable when depolarized with a high KCl solution. At (C), pharmacologically blocking P2X3 receptors with the selective antagonist AF-353 in cultured mouse nociceptors reversibly blocks the venom- and α,β,Me-ATP-elicited calcium responses. At (D), it is shown that the blockade of P2X3 receptors to Emodin also prevents nociceptors from getting activated by the lionfish venom.

Exemplary Study 5:

It is further demonstrated that blocking the P2X3 receptor in humans can result in alleviating or eliminating pain in human subjects.

To verify the efficacy of this compound in humans, dorsal root ganglia were isolated from human organ donors and placed in culture between 3 and 5 hours after cross-clamping the heart. Sensory neurons were cultured for at least 5 days before performing any experiments to allow for satellite cell detachment. For calcium imaging experiments, human nociceptors were exposed to the lionfish venom in the presence of the P2X3 receptor antagonist AF-353 (300 nM), which was introduced in the bath solution (in mM: NaCl 150, KCl 3, Glucose 10, $CaCl_2$) 2, and MgCl2 1; in distilled water, buffered to a pH of 7.3). Cells were incubated with AF-353 for 8-minutes either after an initial application of lionfish venom or before any applications of the venom. Venom was applied in 2-second puffs with a picospritzer as in FIG. 2.

Figure 5:
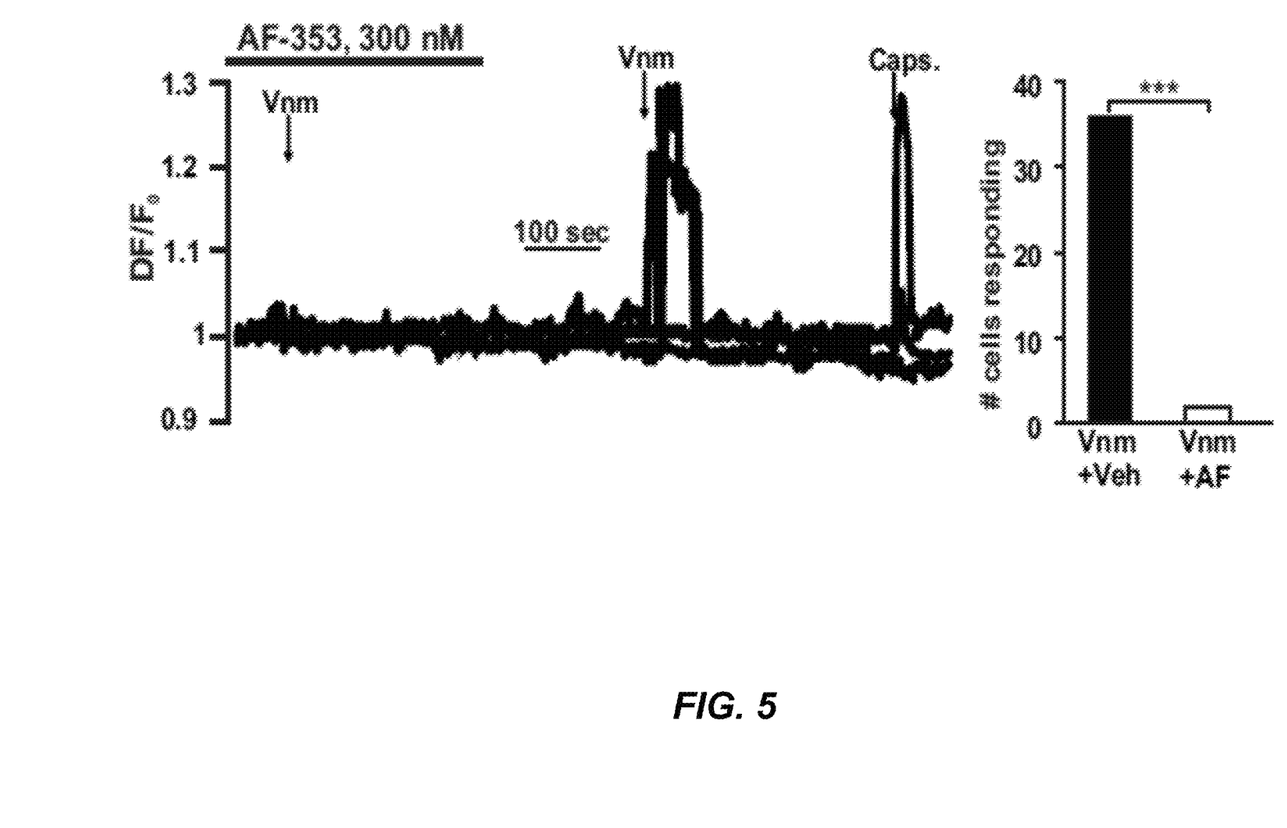
FIG. 5 shows graphs demonstrating that blocking the same receptor in human nociceptors can also protect them from the excitatory effect of the venom.

As shown in FIG. 5, in the left panel, in the presence of the antagonist, human nociceptors do not display calcium responses upon exposure to lionfish venom. However, after wash-out of the antagonist, venom-induced calcium responses appear. Furthermore, these responses do not occur in cells which are capsaicin-sensitive, indicating that the venom seems to preserve its specificity for non-peptidergic, TRPV1-negatic sensory neurons in humans and confirming the observations made in mouse nociceptors. In the right panel, it is shown that quantification of the proportion of human sensory neurons responding to lionfish venom in the absence and presence of lionfish venom. (*** indicates $p<0.001$ by Fisher's exact test).

As such, this shows that blocking the P2X3 receptors would also alleviate and/or eliminate the pain symptoms caused by lionfish envenomation.

Exemplary Study 6:

It is then demonstrated that P2X3 antagonists are also efficient at blocking the pain caused by lionfish venom in vivo, indicating that these compounds are viable for treating pain following a lionfish envenomation.

AF-353 was prepared in a stock solution of 300 mM in DMSO and diluted to 3 mM in physiological saline for at the time of experimentation. Mice were injected with AF-353 intraplantarly either 30 minutes prior to injection of lionfish venom, to determine whether the compound could be used as a prophylactic treatment against lionfish envenomations, or immediately (within 2 minutes) after injection of lionfish venom in the paw, in order to determine whether the compound could be used as a treatment after lionfish envenomations. During the experiment, mice were placed on a glass surface with a mirror placed underneath at a 45-degree angle and kept in round Plexi-glass restrainers. A video camera filmed the animals' spontaneous pain behaviour for an hour. The amount of time the mice spent licking their paws was quantified by two independent and blinded experimenters.

Figure 6:
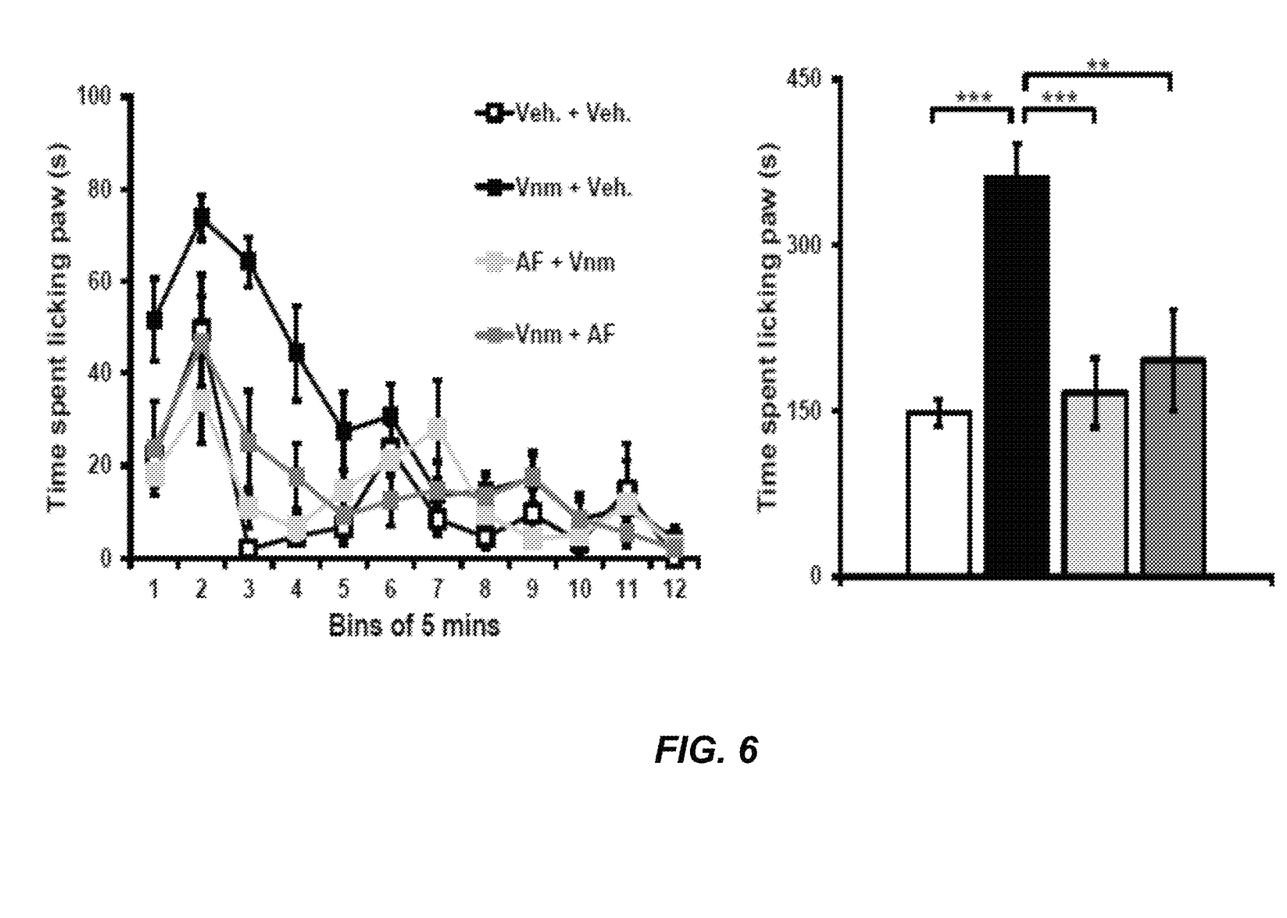
FIG. 6 shows graphs that demonstrate that P2X3 antagonists are also efficient at blocking the pain caused by lionfish venom in vivo, indicating that these compounds are viable for treating pain following a lionfish envenomation.

As illustrated in FIG. 6, the left panel shows the mean (±sem) time spent licking the venom-injected paw per 5-minute bin by the injected mice. Mice were injected with the vehicle (Veh) for AF-353 (DMSO) 30 minutes prior to injection of the Veh for the venom (physiological saline) (empty squares), venom (Vnm) followed by Veh (DMSO; black squares), AF-353 (AF, 3 mM in a total volume of 20 μL) followed by venom (light grey squares), or venom followed by AF-353 (dark grey squares). n=5 mice per group. The dose of venom injected was 66 μg of crude venom in a total volume of 20 μL (veh. saline). The right panel: shows the quantification of the left panel, displaying the total time spent licking the injected paw during a 1-hour period. Stats: *=P<0.001; =P=0.009. Unpaired t test.

Exemplary Study 7:

It was then demonstrated that local administration of a formulation containing Emodin, another pharmacological antagonist of P2X3, can block the pain caused by the injection of the lionfish venom.

This formulation was prepared in distilled water, and the final concentrations of all components were: 4% Lidocaine-hydrochloride, 200 μM EDTA, 2% Tromethamine at 5 mg/kg Emodin. The solution was prepared on the day of the experiment. Controls were performed by injecting vehicle (20 μL distilled water+DMSO). Mice were injected with this formulation intraplantarly immediately after venom injection (66 μg dose of crude venom in a total volume of 20 μL) to determine whether this cocktail would serve as an efficient remedy for the pain following lionfish envenomations. To determine the amount of pain felt by the mice, a spontaneous pain assay was performed as described in FIG. 6.

Figure 7:
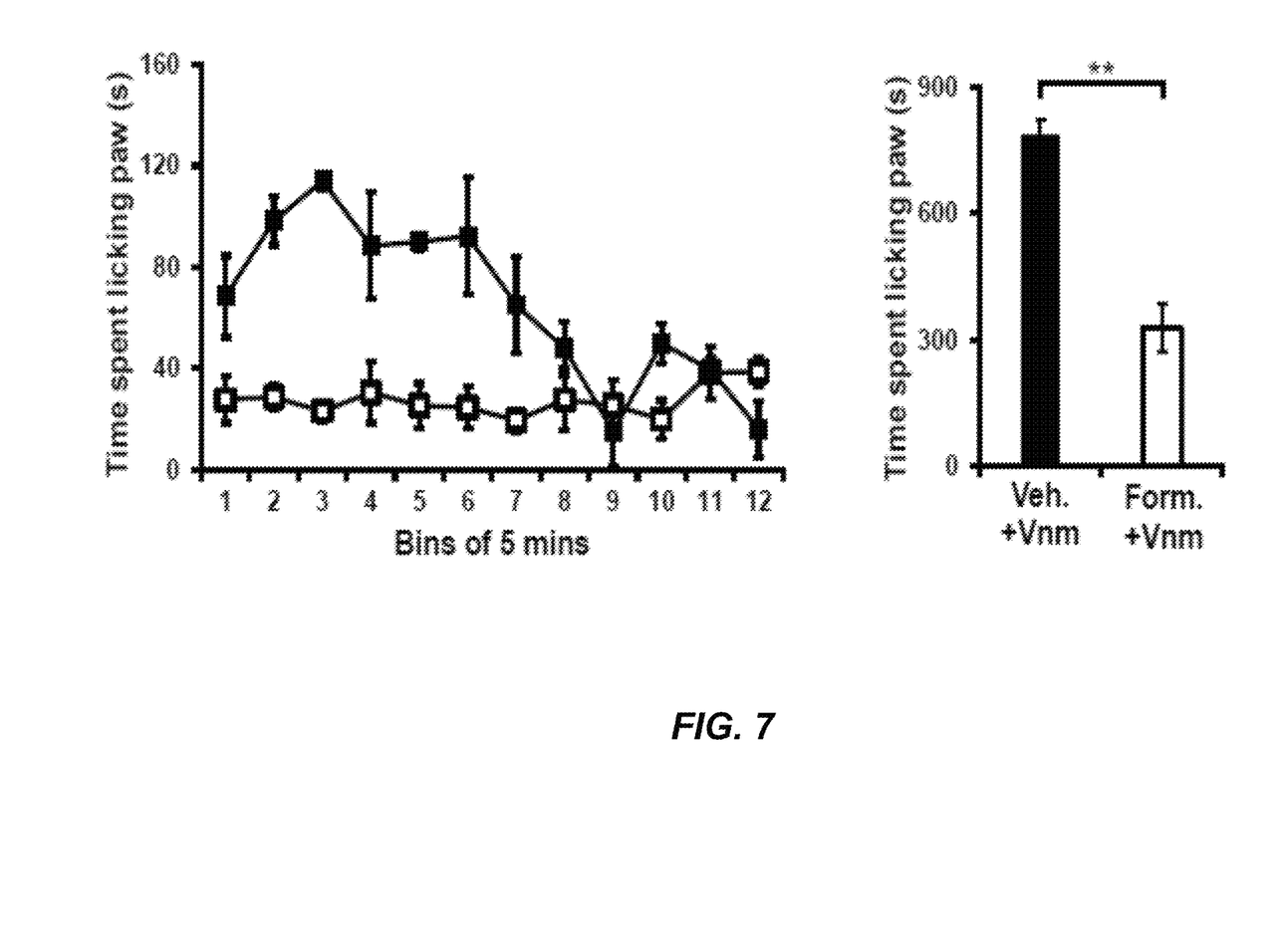
FIG. 7 shows graphs that demonstrate that local administration of a formulation containing Emodin, another pharmacological antagonist of P2X3, can block the pain caused by the injection of the lionfish venom.

As illustrated in FIG. 7, the left panel shows the mean (±sem) time spent licking the venom-injected paw per 5-minute bin. Mice that received the emodin-containing formulation experienced less pain over time than those that did not receive the emodin-containing formulation. The right panel shows the sum of the amount of time mice spent licking their paws in an hour after injections. Overall, mice injected with the formulation exhibited significantly less pain behaviour than those that did not receive the formulation. Stats: **=p=0.00128, Unpaired t test.

As such, it is demonstrated that different P2X3 receptor antagonists may be used to reduce the pain resulting from lionfish envenomation. One or more P2X3 receptor antagonists may be used. The present disclosure provides other exemplary P2X3 receptor antagonists that may be used to treat lionfish envenomation.

Although the invention has been described with reference to preferred embodiments, it is to be understood that modifications may be resorted to as will be apparent to those skilled in the art. Such modifications and variations are to be considered within the purview and scope of the present invention.

Representative, non-limiting examples of the present invention were described above in detail with reference to the attached drawing. This detailed description is merely intended to teach a person of skill in the art further details for practicing preferred aspects of the present teachings and is not intended to limit the scope of the invention. Furthermore, each of the additional features and teachings disclosed above and below may be utilized separately or in conjunction with other features and teachings.

Moreover, combinations of features and steps disclosed in the above detailed description, as well as in the experimental examples, may not be necessary to practice the invention in the broadest sense, and are instead taught merely to particularly describe representative examples of the invention. Furthermore, various features of the above-described representative examples, as well as the various independent and dependent claims below, may be combined in ways that are not specifically and explicitly enumerated in order to provide additional useful embodiments of the present teachings.

What is claimed is:

1. A method of relieving, inhibiting or arresting pain from lionfish envenomation comprising administering to skin of a subject a topical of parenteral formulation comprising a therapeutically effective amount of a P2X3 receptor antagonist, wherein the therapeutically effective amount has been calculated to be sufficient to reduce activation of non-peptidergic, TRPV1-negative nociceptors at the skin of the subject.

2. The method as defined in claim 1, wherein the antagonist of the P2X3 receptor comprises a compound of the following formula:

or a pharmaceutically acceptable salt thereof.

3. The method as defined in claim 1, wherein the lionfish is of a species *Pterois volitans*.

4. The method as defined in claim 1, wherein the antagonist is administered within the first two hours following the lionfish envenomation.

5. The method as defined in claim 4, wherein the antagonist is administered within the first thirty minutes following the lionfish envenomation.

6. The method as defined in claim 1, wherein the antagonist is administered within an hour prior to the subject entering water where lionfish may be located.

7. The method as defined in claim 1, following the lionfish envenomation, further comprising at least one of disinfecting or applying an antiseptic to a site of the subject where the subject has been stung by the lionfish.

8. The method as defined in claim 1, following the lionfish envenomation, further comprising submerging a body part of the subject that has been stung by the lionfish in hot water of at least 40° C.

9. The method as defining in claim 1, further comprising re-administering, within two hours following a last administration of the P2X3 receptor antagonist, an additional therapeutically effective amount of the P2X3 receptor antagonist.

10. The method as defined in claim 1, following the lionfish envenomation, wherein the administration is performed by injection at or near a site where the subject was stung by the lionfish.

* * * * *

UNITED STATES PATENT AND TRADEMARK OFFICE
CERTIFICATE OF CORRECTION

PATENT NO. : 11,278,504 B1
APPLICATION NO. : 16/856688
DATED : March 22, 2022
INVENTOR(S) : Sharif Naeini et al.

It is certified that error appears in the above-identified patent and that said Letters Patent is hereby corrected as shown below:

In the Specification

1. In Column 10, Line 21, delete "ciano," and insert -- cyano, --, therefor.

2. In Column 14, Line 63, delete "subthermophlla," and insert -- subthermophila, --, therefor.

3. In Column 17, Line 67, delete "videocamera." and insert -- video camera. --, therefor.

4. In Column 19, Line 58, delete "acetoxymethylester" and insert -- acetoxymethyl ester --, therefor.

5. In Column 21, Line 48, delete "TRPVI-negatic" and insert -- TRPVI-negative --, therefor.

In the Claims

6. In Column 23, Claim 1, Line 13, delete "of parenteral" and insert -- or parenteral --, therefor.

7. In Column 24, Claim 9, Line 21, delete "defining" and insert -- defined --, therefor.

Signed and Sealed this
Twenty-fourth Day of May, 2022

Katherine Kelly Vidal
*Director of the United States Patent and Trademark Office*